(12) United States Patent
Aleo et al.

(10) Patent No.: US 10,342,816 B2
(45) Date of Patent: Jul. 9, 2019

(54) AQUEOUS OPHTHALMIC FORMULATIONS BASED ON AZITHROMYCIN

(71) Applicant: MEDIVIS S.R.L., Catania (IT)

(72) Inventors: Danilo Aleo, Catania (IT); Maria Grazia Antonietta Saita, Catania (IT); Barbara Melilli, Catania (IT); Sergio Mangiafico, Catania (IT); Melina Cro, Catania (IT)

(73) Assignee: MEDIVIS S.R.L., Catania (IT)

( * ) Notice: Subject to any disclaimer, the term of this patent is extended or adjusted under 35 U.S.C. 154(b) by 0 days.

(21) Appl. No.: 14/785,814

(22) PCT Filed: May 6, 2014

(86) PCT No.: PCT/IT2014/000120
§ 371 (c)(1),
(2) Date: Oct. 20, 2015

(87) PCT Pub. No.: WO2014/181368
PCT Pub. Date: Nov. 13, 2014

(65) Prior Publication Data
US 2016/0074426 A1   Mar. 17, 2016

(30) Foreign Application Priority Data
May 6, 2013   (IT) .............. RM2013A0268

(51) Int. Cl.
*A61K 31/7052* (2006.01)
*A61K 9/00* (2006.01)
*A61K 47/69* (2017.01)

(52) U.S. Cl.
CPC ........ *A61K 31/7052* (2013.01); *A61K 9/0048* (2013.01); *A61K 47/6951* (2017.08); *Y02A 50/478* (2018.01)

(58) Field of Classification Search
None
See application file for complete search history.

(56) References Cited

U.S. PATENT DOCUMENTS

2005/0215520 A1* 9/2005 Liu ............... A61K 9/0019
514/58
2009/0312724 A1* 12/2009 Pipkin ............. A61K 9/0043
604/294

FOREIGN PATENT DOCUMENTS

WO  WO 2008/025560 A1   3/2008
WO  WO 2009/003199 A1   12/2008

OTHER PUBLICATIONS

International Search Report of International Patent Application No. PCT/IT2014/000120 dated Oct. 9, 2014.
Italian Search Report of Italian Patent Application No. RM20130268 dated Jan. 8, 2014.

* cited by examiner

*Primary Examiner* — Shaojia A Jiang
*Assistant Examiner* — Dale R Miller
(74) *Attorney, Agent, or Firm* — Arent Fox LLP

(57) ABSTRACT

The invention concerns topical ophthalmic preparations in the form of eye-drops in aqueous solution, containing azithromycin (or a pharmacologically acceptable salt thereof) as active ingredient, wherein the azithromycin is solubilized and stabilized by means of β-cyclodextrins, and in particular by means of the β-cyclodextrin called sulfobutyl ether β-cyclodextrin (SBE-β-CD).
The proposed preparations have a remarkably high stability, both physical and chemical, which enables its storage at room temperature for the envisaged period of validity for a commercial pharmaceutical product.

11 Claims, 1 Drawing Sheet

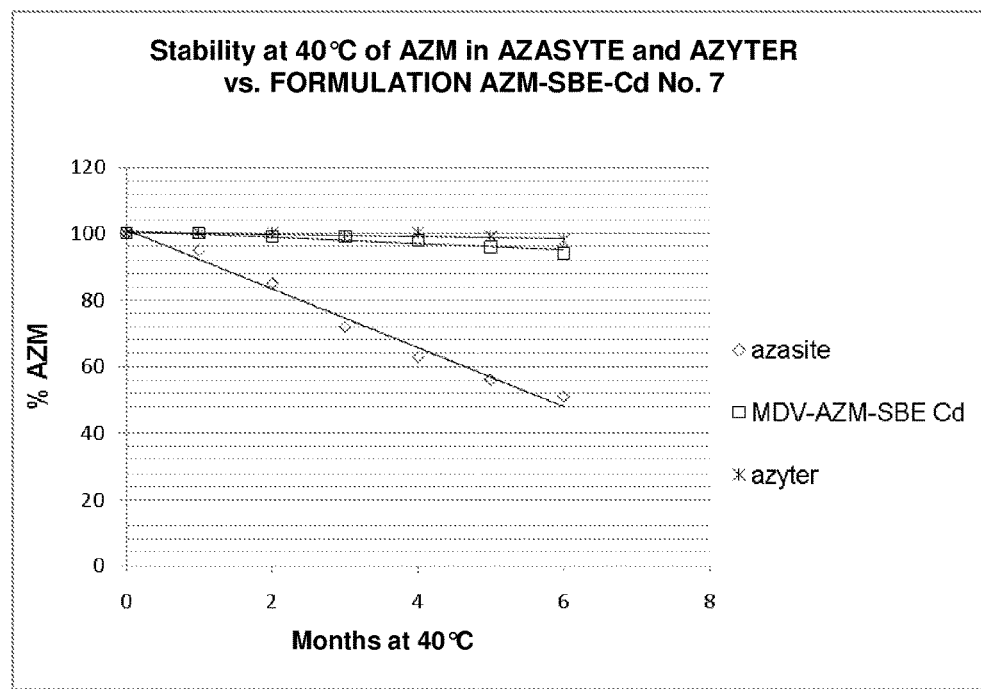

AQUEOUS OPHTHALMIC FORMULATIONS BASED ON AZITHROMYCIN

CROSS-REFERENCED TO RELATED APPLICATION

This application is a National Phase entry of International Application PCT/IT2014/000120, filed May 6, 2014 which claims priority to Italian Patent Application No. RM2013A000268, filed May 6, 2013. The disclosure of the prior application is hereby incorporated in its entirety by reference.

FIELD OF THE INVENTION

The present invention relates to aqueous ophthalmic formulations based on azithromycin. More specifically, the invention concerns stable preparations for topical ophthalmic use in the form of eye drops in aqueous solution containing azithromycin (or a pharmaceutically acceptable salt thereof) as the active ingredient, solubilized and stabilized in the presence of cyclodextrins, in particular the β-cyclodextrin known as sulfobutyl ether-β-cyclodextrin (SBE-β-CD). The proposed preparations show a remarkably high stability, both physical and chemical, which allows their storage at room temperature for the shelf-life period required for commercial pharmaceutical products.

BACKGROUND OF THE INVENTION

As is known, azithromycin is a semisynthetic antibiotic belonging to the family of macrolides, whose parent is erythromycin, a natural antibiotic produced by fermentation by *Streptomyces erythraeus*. Macrolides are defined in general as a group of pharmacologically active molecules containing a macrolide ring, i.e. a macrocyclic lactone ring (generally having 14-16 members) to which one or more deoxy sugars can be connected. The biological activity of such compounds is linked to their ability to inhibit the biosynthesis of bacterial proteins.

The need to obtain macrolides more powerful and more chemically stable than erythromycin was the reason that led to the development of azithromycin (hereinafter also referred to by the acronym AZM). The chemical change consisted in the replacement of a keto group with a methylamino group on the lactone ring of erythromycin, so as to obtain a cyclic compound with a nitrogen atom inserted in the macrolide ring, as shown in the structural formula below:

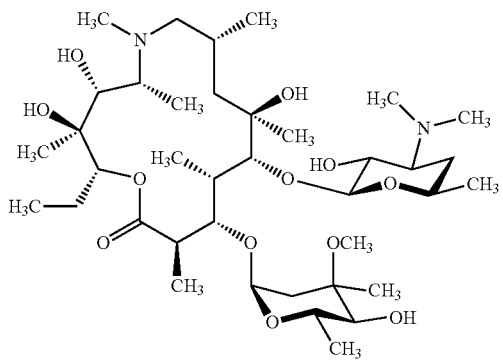

Azithromycin (AZM)

Said chemical change improved the chemical, pharmacokinetic and microbiological profile of this macrolide with respect to the starting erythromycin. The semi-synthetic macrolide compounds which have the aforementioned substitution, named azalides, have improved pharmacokinetic properties and greater stability characteristics with respect to the starting macrolide: For this reason azithromycin is currently more widely used compared to erythromycin (Fiese, E. F., Steffen, S. H., Comparison of the acid stability of azithromycin and erythromycin A, *J. Antimicrob. Chemother.*, January 1990, Suppl A:39-47).

Azithromycin also shows a broader spectrum of activity than the other macrolides, having a better antibacterial activity on Gram-positive bacteria, and also extending such activity to Gram-negative bacteria. In view of that azythromycin has become the drug of choice in the treatment of soft tissue infections caused by *Chlamydia pneumoniae, Chlamydia trachomatis, Legionella pneumophila, Moraxella catarrhalis, Mycoplasma hominis, Mycoplasma pneumoniae, Neisseria gonorrhoeae, Peptostreptococcus* species, *Streptococcus pyogenes, Streptococcus agalactiae*, streptococci of groups C, F and G, *Ureaplasma urealyticum, Haemophilus influenzae*, etc. The pharmacokinetic profile is enhanced compared to that of erythromycin, as after oral administration a higher intracellular distribution and a longer plasma half-life ensues, thereby allowing once-daily dosing (Gladue, R. P., In vitro and in vivo uptake of azithromycin (CP-62,993) by phagocytic cells: possible mechanism of delivery and release at sites of infection, *Antimicrob. Agents Chemother*. March 1989, 33: 277-82; Ball, A. P. Azithromycin: an interim analysis, *J. Int. Med. Res*. November-December 1991, 19 (6):446-50). All of these factors have contributed to the success of azithromycin on erythromycin, making such active ingredient one of the antibiotic drugs most widely marketed worldwide.

Despite its excellent pharmacokinetic characteristics and the broad spectrum of action, AZM has been used, to date, mostly through the oral and parenteral routes of administration. Quite a high number of preparations based on AZM are presently on the market in the form of tablets, capsules, powders for injectable products and oral suspensions, whereas for topical ophthalmic applications azithromycin has not yet found a comparably large use. For the treatment of bacterial and trachomatous diseases affecting the ocular surface, the specialists in the field have not had available, for a long time after its introduction on the market (dating back to the early '80s), a topical ophthalmic product having AZM as active ingredient: Thus, they had to resort to oral systemic therapies to eradicate ocular infections and treat infectious diseases such as bacterial conjunctivitis, uveitis, superficial and interstitial ulcers, post-operative infections, keratitis and blepharitis (Andrews, V., Antibiotic treatment of ophthalmic infection: new developments, *J. Hospital Infection* 1995, 30: 268-274).

In this regard, it is known that administration through the topical ophthalmic route is preferable in order to avoid both problems of systemic absorption, and therefore toxicity, and the onset of drug resistance. This need is more urgent after the warning issued by the FDA in March 2013, on the systemic use of azithromycin in connection with cases of cardiac arrhythmias. In addition, although it is known in the literature that azithromycin following oral administration reaches significant concentrations in the lachrymal gland and conjunctiva, the available data indicate that in order to reach the MIC (Minimum Inhibitory Concentration) following topical ophthalmic administration it is nevertheless necessary to formulate the systemic AZM at high concentrations (Tabbara, K. F., Ocular level of azithromycin, *Arch. Ophthalmol.* 1998, 116 (12), 1625-1628; Kargioglu, Z. A., Pharmacokinetics of azithromycin in trachoma patients: serum and tear level, *Ophthalmic Res.* 1999, 31 (1), 47-52; I. Cochereau, I., Efficacy and safety of short duration azithromycin eye drops versus azithromycin single oral dose for the treatment of trachoma in children: a randomised, controlled, double-masked clinical trial, *Br. J. Ophthalmol.* 2007, 91:667-672).

The lack of AZM preparations administrable through the topical ophthalmic route is due to the physico-chemical characteristics of the azalide molecule itself. Indeed, the scientific and patent literature describes azithromycin as a molecule having a low level of solubility and a limited chemical stability in aqueous medium, which is notoriously considered to be the vehicle of choice of ophthalmic preparations. The pharmacopoeia reports that AZM is poorly soluble in water, while it is soluble in almost all organic solvents.

The first topical ophthalmic product based on AZM for the treatment of ocular bacterial infections has been placed on the market in the USA, upon approval of the FDA, in 2007, under the trade name Azasite®. This product is based on a number of patents owned by InSite Vision Inc. and licensed to Inspire Pharmaceuticals Inc. (a subsidiary of Merck & Co.), and on a patent owned by Pfizer, specifically the patents U.S. Pat. Nos. 6,159,458, 6,239,113, 6,569,443 and 7,056,893 assigned to InSite Vision and U.S. Pat. No. 6,861,411 assigned to Pfizer.

The first one of these documents is connected to some earlier patents of the same company (such as the U.S. Pat. No. 5,192,535), and concerns the production of ophthalmic release forms based on matrices of moderately crosslinked carboxylic polymers (polycarbophil), which allow to obtain a sufficiently low viscosity in order to be easily administered in the form of eye drops, and which then form a mucoadhesive gel in the eye, in order to retain the drug delivered in the site of administration for prolonged periods. The patent text refers in particular to water-soluble active ingredients, and cites pilocarpine as the preferred example.

The second and third documents (which in fact correspond to a single international patent application, Publ. No. WO00/57866 assigned to InSite Vision), concern the application of the teachings of previous patents of the same holder to the specific case of azithromycin, an active ingredient insoluble in water, which can be kept in suspension in the polymeric vehicle with delivery systems such as those mentioned above, stable from the physical point of view. The polymer delivery system proposed by the cited patents of InSite Vision is commercially known as DuraSite® (polycarbophil, disodium edetate, sodium chloride).

The Pfizer patent on which the drug Azasite® is based, U.S. Pat. No. 6,861,411, having title "Method for the treatment of eye infections with azithromycin" (and corresponding to European patent EP 0924789), reaffirms the potent antibacterial activity of azithromycin compared with erythromycin, gentamicin or other ophthalmic antibiotics, which makes it possible to implement the antibiotic therapy with a single daily administration rather than 4-6 daily doses prescribed for other ophthalmic antibiotic. The azithromycin compositions disclosed have a concentration of from 0.5 to 2.5%, and azithromycin can be formulated therein in one of the following forms:

isotonic solution at pH 7-8, in the presence of a suitable buffer (in particular borate buffer) and a tonicity adjusting agent (in particular glycerin);

in dispersed form in a matrix of white vaseline, liquid paraffin and lanolin to provide salves and ointments;

suspended in a gel thanks to the use of polyacrylic polymers, such as Carbopol.

The third solution is actually adopted in the Azasite ophthalmic pharmaceutical product, while the other two appear to somehow represent theoretical possibilities, the first one because of the substantial insolubility of azithromycin in water, and the second due to poor patient compliance in respect of oily semisolid products such as ointments and salves for ophthalmic application. It should be noted that the text of the document does not mention any commercial preparations that can meet the stability requirements, both physical and chemical, of a pharmaceutical product, as the patent is confined to the general proposal of the therapeutic method.

The fourth US patent of InSite Vision connected to the commercial product Azasite, U.S. Pat. No. 7,056,893 of InSite Vision, finally addresses the problem of stability of the preparation of azithromycin, and proposes a pH range between 6.0 and 6.5, preferably 6.3, in which the AZM molecule is more stable. Stability studies carried out to the preservation at 25° C. and 4° C. have been reported for a period of 6 months, while for the stability studies at 40° C. are reported for up to two months, and the title of AZM is about 90% of its initial value for the best formulations, at pH 6.0 and 6.5.

From the table of stability, which can be derived from a check of the active content in the AZM formulations in DuraSite® over the 6 months, the impossibility of storing such product it at room temperature is evidente, as the formulation stored at 25° C. has a 92% of active after six months. These results highlight the need for a storage in refrigerated conditions, in order to slow down the kinetics of chemical degradation.

In a scientific work connected to the research on AZM formulations in a gelling polymer vehicle of the type of DuraSite® (Esteban, S. L., Manzo, R. H., Alovero, F. L., Azithromycin loaded on hydrogels of carbomer: chemical stability and delivery properties, *Int. J. Of Pharm.* 2009, 366, 53-57) the increased chemical stability of the azalide in the presence of polyacrylic polymers (Carbopol) is evidenced, compared to a formulation of AZM in phosphate buffer. In this article the greater stability of the AZM-Carbopol systems is ascribed to some electrostatic interactions between the basic functions of AZM and the acid functions present in the polymer, in agreement with what is schematically shown below:

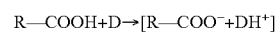

$$R\text{—}COOH + D \rightarrow [R\text{—}COO^- + DH^+]$$

wherein RCOOH represents the polyacrylic polymer, rich of carboxy moieties, and D represents the drug, having at least one basic group. This phenomenon has been interpreted by hypothesizing that a negative electrokinetic potential capable of creating a microenvironment with a pH lower than that of the solution, unfavorable to hydrolysis, is established. A similar behavior has also been observed for procaine formulated in a Carbopol gel.

The only other ophthalmic pharmaceutical product for topical use based on azithromycin is currently the eye-drops product sold in Europe under the trade name Azyter® (Laboratoires Théa), based on the European patent EP 1377316 (and other patents of the same family, including U.S. Pat. No. 7,064,109), relating to a formulation of AZM (1.5% in the preferred embodiment) in an oily vehicle formed by fatty acid triglycerides The inventors of the patent on Azyter recall in this document the limitations associated with the use of suspensions in ophthalmology. In fact, if on one hand the pre-corneal retention time the of the particles of active ingredient increases, on the other hand the foreign body sensation on the ocular surface is inevitable. This unpleasant effect is more pronounced during an inflammatory process, causing by itself irritation of the ocular mucosae, in addition to uncertainty about the uniformity of dosage. According to the cited document, an ophthalmic formulation having azithromycin dissolved in an oily medium, preferably consisting of medium-chain triglycerides (MCT), solving the problem of solubility by excluding water as a vehicle, allows to avoid this drawback.

Still according to the Théa patent, the type of formulation selected also allows to increase the residence time, and therefore the precorneal bioavailability, of azalide on ocular structures, as the thin layer of "medicated oil" persists longer on the ocular surface than does an aqueous solution. In substance, in order to solve the problem related to the stability of azithromycin the inventors had to resort to the use of a non-aqueous vehicle, thanks to which Azyter is storable at 25° C. for 18 months without any need to be stored in a refrigerator.

In order to have a good compliance, an ophthalmic formulation must have a composition, in terms of aqueous vehicle, neutral pH, salt composition, value of surface tension and viscosity as similar as possible to those of the tear fluid. Therefore, it will be appreciated that an oily vehicle such as the one described in the cited patent has characteristics quite different from the optimal ones of an antibiotic in eye drops. In fact, its administration could cause blurred vision, discomfort and temporary burning sensation to the patient. If it is considered that the recipients of the therapy include pediatric patients, it will be apparent that a therapy with the eye drops proposed is not easy to manage.

As mentioned above, the main problems related to the formulation of azithromycin in water are linked to the following:
the very low water solubility of the molecule,
its susceptibility to degradation in an aqueous medium.

It has been shown that the main mechanism of degradation of azithromycin is the hydrolysis of the 1,4 α-glucosidic bond, which leads to cleavage of the sugar bound to C3 (L-cladinose) and to a microbiologically inactive metabolite (desosaminyl-azithromycin, DAZM), according to the scheme described below:

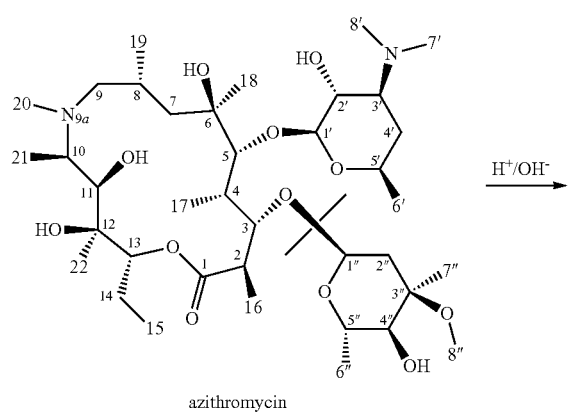

azithromycin

H⁺/OH⁻ →

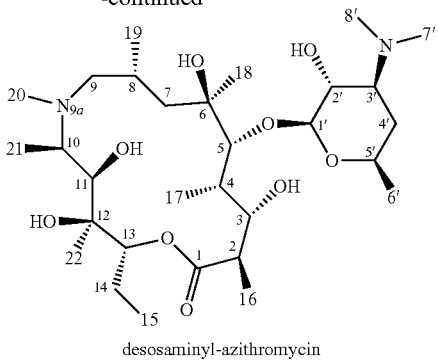

desosaminyl-azithromycin

Many studies have been carried out to devise the best experimental conditions to slow down this phenomenon, and in particular both the ionic strength and the type of buffer system have been investigated, as well as the pH. Zhang and co-workers (Zhang. Y. et al., Aspect of degradation kinetics of azithromycin in aqueous solution, *Chromatographia* 2009, 70 (1/2, 67-73)) show that the kinetics of the hydrolytic phenomenon has the minimum value at pH 6.3 (as noted in U.S. Pat. No. 7,056,893), especially in the presence of a phosphate buffer and a low ionic strength, while it seems not to be influenced by the initial macrolide concentration. Being the degradation linked to a hydrolytic problem, and since water is the vehicle of choice of ophthalmic formulations, the difficulty linked to the problem of formulating azithromycin in an aqueous medium for a commercial preparation to be proposed for storage at 25° C. is self-evident.

In view of the foregoing, there appears to be an evident need to have available a pharmaceutical preparation in eye-drops containing azithromycin as the active ingredient, and being:
in an aqueous vehicle, stable at 25° C., and suitable for storage at room temperature for at least 24 months;
well tolerated by the patient.

SUMMARY OF THE INVENTION

In the frame of the studies that led to the present invention the possibility of solubilizing azithromycin by means of cyclodextrins has been considered.

As is well known, cyclodextrins (CDs) are natural cyclic oligosaccharides of toroidal shape, composed of 6, 7 or 8 α-(1,4)-glucopyranoside units, derived from starch. They possess a central lipophilic cavity, which can accommodate various types of hydrophobic molecules (guest) while the outer surface, on which the hydroxy groups of the oligosaccharide are arranged, has hydrophilic properties, and gives it a good solubility in water. When a molecule of suitable polarity and size is housed in the cavity of the CD an interaction with the guest molecule occurs, according to a specific guest-host type "molecular recognition", with formation of an inclusion complex.

While α-cyclodextrins, consisting of 6 monomer units, do not find a large use in the pharmaceutical industry in view of the small size of their cavity, β-cyclodextrins (7 monomer units) and, to a lesser extent, γ-cyclodextrins (8 monomer units) are often used in the pharmaceutical field, thanks to the size of their lipophilic cavity and to their great safety of use. In addition to natural oligosaccharide compounds, variously functionalized forms of cyclodextrins, endowed with characteristics different from one another depending on the intended purposes, have also been designed.

Aqueous eye-drops products already on the market, in which the cyclodextrins are used as excipients to increase the solubility of the active ingredient, include Indocid® (indomethacin), employing β-hydroxypropyl-cyclodextrin; Clorocil® (chloramphenicol), employing variously methylated β-cyclodextrins, and Voltaren Ophtha® (sodium diclofenac), employing 2-hydroxypropyl-γ-cyclodextrin.

More recently, medicinal products for systemic administration based on another type of functionalized beta-cyclodextrin have been developed, called 2-sulphobutyl ether β-cyclodextrin (SBE-β-CD), where a number of hydroxy groups on the glucopyranose units are functionalized with sulphobutylether groups. A representative of SBE-β-CD is the cyclodextrin known under the trade name Captisol™. The latter was used in Vfend® (voriconazole), a triazole antifungal drug for intravenous administration, and in Geodon®/Zeoldox® (ziprasidone mesylate), an antipsychotic for intramuscular injection. The primary, and best known, mechanism through which cyclodextrins solubilize a lipophilic molecule is the formation of soluble inclusion "CD-guest" complexes, but recently other phenomena have been observed showing that in certain conditions cyclodextrins also give rise to supramolecular aggregates (nano-aggregates) (Loftsson, T, Cyclodextrins and their pharmaceutical applications, $Int. J. of Pharm.$ 2007, 329 1-11).

According to the present invention, it has now been found that it is possible to obtain an aqueous ophthalmic formulation for topical use containing azithromycin thermally stable and well tolerated, which can be proposed for a storage at 25° C., using a stabilizing/solubilizing system consisting of beta-cyclodextrins functionalized with sulfoalkyl ether groups, in a pH range between 6.0 and 7.6. In particular, sulfobutyl ether beta-cyclodextrin, SBE-β-CD, has been shown to be capable of solubilizing AZM to the levels required for administration in aqueous eye-drops, and turned out to be particularly suitable for preparations to be stored at room temperature, having provided surprising results in the stabilization of azithromycin in aqueous solution.

It has actually been found that azithromycin in the formulations developed in accordance with the invention is not only readily soluble, but also significantly more stable than in the commercial product in aqueous eye-drops Azasite, if placed in the same storage conditions. Using the sulfobutyl ether-cyclodextrin formulation as a starting point, other formulations have been developed by the addition of various excipients, such as viscosifying and mucoadhesive polymers, tonicity adjusting agents, buffers and any antioxidants, and the addition of these excipients did not change the chemical stability profile of azithromycin, nor its physical stability, no precipitation phenomena for the duration of storage of the product having been observed.

The aqueous formulations of AZM particularly stable and suitable for administration in the eye in the form of eye-drops are characterized, according to the present invention, by a content of AZM between 0.5 and 2.5% by weight, with a pH between 6.0 and 7.6 and a content of sulfoalkyl ether beta-cyclodextrin, preferably of SBE-β-CD, between 2% and 15% by weight.

DETAILED DESCRIPTION OF THE INVENTION

The present invention, therefore, specifically concerns a topic ophthalmic preparation in aqueous solution containing azithromycin as active ingredient, solubilized and stabilized with a sulfoalkyl ether beta-cyclodextrin (SAE-β-CD), said preparation having a pH comprised between 6.0 and 7.6 and a concentration of azithromycin, or of a pharmacologically acceptable salt or hydrate thereof, comprised between 0.5 and 2.5% by weight. Specifically, the sulfoalkyl ether beta-cyclodextrin can be a sulfomethyl, sulfoethyl, sulfopropyl or sulfobutyl ether β-cyclodextrin, or also a sulfopentyl or sulfohexyl ether 3-cyclodextrin, according to the length of the alkyl chains with which the original cyclodextrin has been functionalized.

Preferably, the sulfoalkyl ether beta-cyclodextrin employed in the proposed ophthalmic solution is a sulfobutyl ether-β-cyclodextrin (SBE-β-CD), and, specifically, it is the beta-cyclodextrin known with the commercial name Captisol™.

Preferably, said SBE-β-CD is present in solution at a concentration of from 2% to 15% by weight and, according to a preferred embodiment of the invention, the weight ratio of said SBE-β-CD and azithromycin is between 2.5:1 and 10:1.

According to some preferred formulations of the topical ophthalmic preparation of the invention, the concentration of azithromycin may be comprised between 1.0 and 2.5% by weight, and particularly preferably manner it is from 1.0, to 1.5% by weight.

According to some specific embodiments of the invention, the pH of the ophthalmic solution is in the range between 6.6 and 7.4 and, particularly preferably, the concentration of sulfobutyl ether-β-cyclodextrin (SBE-β-CD), is between 4% and 10% by weight.

The composition according to the invention generally comprises tonicity adjusting agents such as NaCl, glycerol, mannitol and trehalose, at concentrations such as to bring the osmolarity of the preparation in the range of physiological values and, in addition, an ophthalmically acceptable buffer system such as citrate, phosphate buffer or borate buffer, and among these, preferably, the phosphate buffer.

In order to increase the precorneal retention time of the eye drops according to the invention, and therefore the bioavailability of the azalide, mucoadhesive polymers can be included in the formulation, including hyaluronic acid and acrylic polymers such as the carbopols and/or modified carbopols (Pemulen), whose mucoadhesivity is described in the literature. Yet, also viscosifying agents such as polyvinyl alcohols (PVA) and various cellulose products (carboxycellulose, hydroxypropyl cellulose, etc.).

Therefore, according to some preferred embodiments of the present invention the proposed topical ophthalmic preparation may include a viscosifying and/or mucoadhesive polymer, selected in particular from the group consisting of: carboxymethylcellulose, hydroxypropyl methylcellulose, hyaluronic acid, chondroitin sulfate, alginic acid, natural polysaccharides, dextran, carbomer, carbopol, polyvinyl alcohol, polyethylene glycol, xanthan gum.

Especially in the case in which the product according to the invention is packaged in multidose vials, which are kept for further use after the first opening, the proposed ophthalmic preparation may comprise, in addition, one or more antioxidant, antimicrobial and/or preservative compounds, in particular those selected from the group consisting of: ascorbic acid, sodium metabisulphite, tocopherol acetate, lactoferrin, sodium edetate, benzalkonium chloride, polyhexanide, TPGS.

The present invention also specifically provides a method of preparation of the formulation based on azithromycin solubilized and stabilized in cyclodextrin according to the invention, which is described below in various steps:
1) preparation of a solution containing phosphate buffer and cyclodextrin;
2) addition of the azalide at room temperature until (partial or complete) dissolution;
3) pH control and regulation by the use of appropriate acids or bases—if necessary, waiting for complete dissolution of azithromycin;
4) addition of the appropriate tonicity adjusting agent and, if requested, of preservatives such as EDTA or polyhexanide and, possibly, of antioxidants or other preservatives;
5) addition of a mucoadhesive polymer;
6) addition of water up to the desired weight.

The solution obtained is left under stirring until complete dissolution of all the components and then is sterilely filtered. The formulations of azithromycin proposed according to the invention offer the advantage of allowing sterile filtration without having to resort to the autoclave or to ionizing radiation, as it happens instead for the Azasite formulation, the composition of which is not sterilizable by filtration.

The specific features of the invention, as well as the advantages of the same compared to the solutions of the known art, will become more apparent with reference to the detailed description of some embodiments thereof, given in the following for illustrative purposes only, and the results of the relative experimentation. Some experimental data are also presented in the graph of the attached FIG. 1, which shows the results of a stability testing at 40° C. of an azithromycin formulation stabilized with cyclodextrin according to the invention, in comparison with the stability of the commercial products Azasite and Aziter.

Examples 1-10

Formulation Examples with Sulfobutyl Ether β-Cyclodextrin (SBE-β-CD)

Some formulations of azithromycin, in which the azalide compound is solubilized by means of sulfobutyl ether-β-cyclodextrin (SBE-β-CD), were obtained by following the preparation procedure described above.

The qualitative and quantitative composition of the formulations is shown in the following table.

| | AZM-SBE-β-CD: FORMULATIONS 1-10 | | | | | | | | | |
|---|---|---|---|---|---|---|---|---|---|---|
| Composition | 1 | 2 | 3 | 4 | 5 | 6 | 7 | 8 | 9 | 10 |
| | | | | | % w/w | | | | | |
| AZM•2H$_2$O | 1 | 1 | 1 | 1 | 1.5 | 1.5 | 1.5 | 2.5 | 2.5 | 2.5 |
| SBE-β-CD | 2.5 | 5 | 7.5 | 10 | 5 | 7.5 | 10 | 10 | 10 | 15 |
| NaH$_2$PO$_4$•2H$_2$O | 0.2 | 0.15 | 0.3 | 0.25 | 0.3 | 0.3 | 0.3 | 0.3 | 0.3 | 0.35 |
| Glycerol | 0.5 | — | — | 0.4 | 0.9 | 0.4 | 0.4 | 0.4 | 0.4 | — |
| NaCl | — | 0.3 | 0.3 | — | — | — | — | — | — | 0.2 |
| EDTA—Na$_2$•H$_2$O | 0.05 | 0.05 | 0.05 | 0.05 | 0.05 | 0.05 | 0.05 | 0.05 | 0.05 | 0.05 |
| Pluronic 127 | — | 0.5 | — | — | 0.5 | — | — | — | 0.5 | — |
| HCl q.s to pH | 6.7 | 6.7 | 7.4 | 6.7 | 7.4 | 6.7 | 6.7 | 6.7 | 6.7 | 6.7 |
| Water for injections | 100 | 100 | 100 | 100 | 100 | 100 | 100 | 100 | 100 | 100 |

Examples 11-19

Formulation Examples with Sulfobutyl Ether β-Cyclodextrin (SBE-β-CD) and Viscosifying Polymers In order to develop a formulation of azithromycin having "depot" characteristics the introduction of matrices of highly mucoadhesive polymers was devised, such as, for example, hyaluronic acid (HA), in concentrations between 0.05 and 0.1%.

The formulation examples 11-19, obtained according to the above procedure, are shown in the table below.

| | AZM-SBE-β-CD with mucoadhesives: FORMULATIONS 11-19 | | | | | | | | |
|---|---|---|---|---|---|---|---|---|---|
| Composition | 11 | 12 | 13 | 14 | 15 | 16 | 17 | 18 | 19 |
| | | | | | % w/w | | | | |
| AZM•2H$_2$O | 1 | 1 | 1 | 1.5 | 1.5 | 1.5 | 1.5 | 1.5 | 2.5 |
| SBE-β-CD | 5 | 5 | 7.5 | 10 | 7.5 | 5 | 7.5 | 10 | 15 |
| NaH$_2$PO$_4$•2H$_2$O | 0.3 | 0.3 | 0.3 | 0.2 | 0.3 | 0.3 | 0.3 | 0.3 | 0.35 |
| Glycerol | 0.4 | 0.45 | — | 0.4 | 0.9 | — | — | 0.4 | 0.4 |
| NaCl | — | — | 0.3 | — | — | 0.28 | 0.28 | — | — |
| EDTA—Na$_2$•H$_2$O | 0.05 | 0.05 | 0.05 | 0.05 | 0.05 | 0.05 | 0.05 | 0.05 | 0.05 |
| Hyaluronic acid | 0.05 | — | 0.1 | 0.1 | 0.1 | 0.1 | 0.1 | 0.075 | 0.1 |
| Pemulen | — | 0.05 | — | 0.1 | — | — | — | — | — |
| Carbopol 980 | — | 0.1 | — | — | — | — | — | — | — |
| Pluronic 127 | — | — | — | — | 0.2 | — | 0.5 | — | — |
| HCl q.s to pH | 6.07 | 7.2 | 7 | 6.7 | 6.7 | 6.7 | 6.7 | 7.4 | 6.7 |
| Water for injections | 100 | 100 | 100 | 100 | 100 | 100 | 100 | 100 | 100 |

Examples 20-29

Comparative Formulation Examples with
β-Hydroxypropyl Cyclodextrin (Hp-β-CD)

In the same way as in Example 1, some formulations based on azithromycin wherein the azalide compound is solubilized by means of β-hydroxypropyl cyclodextrin (Hp-β-CD) have been obtained by proceeding for the preparation in the same way shown above.

The qualitative and quantitative composition of the formulations is shown in the following table.

| Composition | AZM-Hp-β-CD: FORMULATIONS 20-29 | | | | | | | | | |
|---|---|---|---|---|---|---|---|---|---|---|
| | 20 | 21 | 22 | 23 | 24 | 25 | 26 | 27 | 28 | 29 |
| | % w/w | | | | | | | | | |
| AZM•2H$_2$O | 1 | 1 | 1.5 | 1 | 1 | 1.5 | 1.5 | 1.5 | 1.5 | 1.5 |
| Hp-β-CD | 2.5 | 5 | 2.5 | 5 | 7.5 | 7.5 | 10 | 10 | 10 | 10 |
| NaH$_2$PO$_4$•2H$_2$O | 0.15 | 0.15 | 0.2 | 0.2 | 0.35 | 0.3 | 0.3 | 0.3 | 0.3 | 0.3 |
| Glycerol | 0.9 | — | — | 0.9 | — | 0.8 | 0.9 | 0.9 | — | — |
| NaCl | — | 0.3 | 0.3 | — | — | — | — | — | 0.28 | 0.28 |
| EDTA—Na$_2$•H$_2$O | 0.05 | 0.05 | 0.05 | 0.05 | 0.05 | 0.05 | 0.05 | 0.05 | 0.05 | 0.05 |
| HCl q.s to pH | 6.7 | 6.7 | 7 | 6.7 | 7 | 6.7 | 6.7 | 7 | 7.4 | 6.7 |
| Water for injections | 100 | 100 | 100 | 100 | 100 | 100 | 100 | 100 | 100 | 100 |

Examples 30-39

Comparative Formulation Examples with
β-Random Methyl Cyclodextrin (β-CD Methylate)

In the same way as in Example 1, some formulations based on azithromycin wherein the azalide compound is solubilized by means of β-random methyl cyclodextrins (β-CD methylate) have been obtained by proceeding for the preparation in the same way shown above.

The qualitative and quantitative composition of the formulations is shown in the following table.

| Composition | AZM-β-CD METHYILATE: FORMULATIONS 30-39 | | | | | | | | | |
|---|---|---|---|---|---|---|---|---|---|---|
| | 30 | 31 | 32 | 33 | 34 | 35 | 36 | 37 | 38 | 39 |
| | % w/w | | | | | | | | | |
| AZM•2H$_2$O | 1 | 1 | 1.5 | 1 | 1 | 1.5 | 1.5 | 1.5 | 2.5 | 2.5 |
| β-CD methylate | 5 | 5 | 7.5 | 2.5 | 2.5 | 7.5 | 5 | 10 | 10 | 15 |
| NaH$_2$PO$_4$•2H$_2$O | 0.2 | 0.15 | 0.3 | 0.2 | 0.3 | 0.3 | 0.3 | 0.3 | 0.3 | 0.3 |
| Glycerol | 0.9 | — | — | 0.9 | 0.9 | 0.9 | 0.9 | 0.9 | — | 0.9 |
| NaCl | — | 0.3 | 0.3 | — | — | — | — | — | 0.28 | — |
| EDTA—Na$_2$•H$_2$O | 0.05 | 0.05 | 0.05 | 0.05 | 0.05 | 0.05 | 0.05 | 0.05 | 0.05 | 0.05 |
| Pluronic 127 | — | — | 0.5 | 0.5 | 1 | 1 | 1 | — | — | 0.5 |
| HCl q.s to pH | 6.7 | 6.7 | 7.4 | 6.7 | 7 | 6.7 | 6.7 | 6.7 | 7 | 6.7 |
| Water for injections | 100 | 100 | 100 | 100 | 100 | 100 | 100 | 100 | 100 | 100 |

Examples 40-49

Comparative Formulation Examples with
γ-Cyclodextrin (γ-Cd)

In the same way as in Example 1, some formulations based on azithromycin wherein the azalide compound is solubilized by means of γ-cyclodextrin (γ-Cd) have been obtained by proceeding for the preparation in the same way shown above.

The qualitative and quantitative composition of the formulations is shown in the following table.

| AZM-γ-CD: FORMULATIONS 40-49 | | | | | | | | | | |
|---|---|---|---|---|---|---|---|---|---|---|
| | 40 | 41 | 42 | 43 | 44 | 45 | 46 | 47 | 48 | 49 |
| Composition | | | | | % w/w | | | | | |
| AZM•2H$_2$O | 1 | 1 | 1 | 1.5 | 1.5 | 1.5 | 1.5 | 2.5 | 2.5 | 2.5 |
| γ-Cd | 2.5 | 5 | 5 | 2.5 | 5 | 7.5 | 10 | 10 | 15 | 15 |
| NaH$_2$PO$_4$•2H$_2$O | 0.2 | 0.15 | 0.3 | 0.2 | 0.3 | 0.3 | 0.3 | 0.3 | 0.3 | 0.3 |
| Glycerol | 0.9 | — | — | 0.9 | 0.9 | 0.9 | 0.9 | 0.8 | 0.7 | 0.7 |
| NaCl | — | 0.3 | 0.3 | — | 0.3 | — | — | — | — | — |
| EDTA—Na$_2$•H$_2$O | 0.05 | 0.05 | 0.05 | 0.05 | 0.05 | 0.05 | 0.05 | 0.05 | 0.05 | 0.05 |
| HCl q.s to pH | 6.7 | 6.7 | 7 | 6.7 | 6.7 | 7.4 | 6.7 | 6.7 | 6.7 | 7.2 |
| Water for injections | 100 | 100 | 100 | 100 | 100 | 100 | 100 | 100 | 100 | 100 |

Examples 50-59

Comparative Formulation Examples with Sulfobuthyl Ether γ-Cyclodextrin (SBE-γ-CD)

In the same way as in Example 1, some formulations based on azithromycin wherein the azalide compound is solubilized by means of sulfobuthyl ether γ-cyclodextrin (SBE-γ-CD) have been obtained by proceeding for the preparation in the same way shown above.

The qualitative and quantitative composition of the formulations is shown in the following table.

| SBE-γ-CD: FORMULATIONS 50-59 | | | | | | | | | | |
|---|---|---|---|---|---|---|---|---|---|---|
| | 50 | 51 | 52 | 53 | 54 | 55 | 56 | 57 | 58 | 59 |
| Composition | | | | | % w/w | | | | | |
| AZM•2H$_2$O | 1 | 1 | 1 | 1.5 | 1.5 | 1.5 | 1.5 | 2.5 | 2.5 | 2.5 |
| SBE γ-Cd | 2.5 | 5 | 5 | 2.5 | 5 | 7.5 | 10 | 10 | 15 | 15 |
| NaH$_2$PO$_4$•2H$_2$O | 0.2 | 0.15 | 0.3 | 0.2 | 0.3 | 0.3 | 0.3 | 0.3 | 0.3 | 0.3 |
| Glycerol | 0.9 | — | — | 0.9 | 0.9 | 0.9 | 0.9 | 0.8 | 0.7 | 0.7 |
| NaCl | — | 0.3 | 0.3 | — | 0.3 | — | — | — | — | — |
| EDTA—Na$_2$•H$_2$O | 0.05 | 0.05 | 0.05 | 0.05 | 0.05 | 0.05 | 0.05 | 0.05 | 0.05 | 0.05 |
| HCl q.s to pH | 6.7 | 6.7 | 7 | 6.7 | 6.7 | 7.4 | 6.7 | 6.7 | 6.7 | 7.2 |
| Water for injections | 100 | 100 | 100 | 100 | 100 | 100 | 100 | 100 | 100 | 100 |

Stability Tests

The checks on variations of azithromycin content were carried out by HPLC for a period of 6 months at 40° C. and for a period of 8 months for 4/25° C. (see Tables 1 and 2 below).

Also in the formulations according to the invention, the main degradation product of AZM is DAZM, and the sum of the relevant amounts satisfies the mass balance.

The most significant stability studies, which give an idea of the potential shown by the formulation according to the invention, are those carried our at 40° C. in parallel with Azasite and also Azyter, to obtain information on the stability at 40° C. of azithromycin in a nonaqueous medium. Very useful data were available since the first months of stability testing.

The experimental data showed a surprising chemical stability of azithromycin in the aqueous vehicle developed according to the invention in the presence of sulfobuthyl ether β-cyclodextrins. These data are reported by way of example for the formulations AZM-SBE Nos. 3, 7, 10, 12 and 19. Such formulations continue to have an active content of between 93 and 95% after 6 months at 40° C., against the 51% of Azasite.

It is also of considerable importance to observe that, among the formulations examined, those with β-cyclodextrin in an appropriate aqueous medium, besides conferring stability to azithromycin, can solubilize high concentrations of azithromycin, i. e. from 0.5 to 2.5%.

Differently, Azasite vehicle is a suspension, presented as an ophthalmic gel and has the advantage of being more acceptable to the patient but, on the other hand, pays this benefit with a lower stability. In fact, the product has a shelf life of 12 months, and must be kept at a temperature of 2-8° C.

TABLE 1

| Stability study at 40° C. 6 months | | | | | | | |
|---|---|---|---|---|---|---|---|
| % AZT in | START | 1 month | 2 months | 3 months | 4 months | 5 months | 6 months |
| AZM-SBE | | | | | | | |
| Form. No 2 | 100 | 100 | 99 | 99 | 98 | 96 | 94 |
| Form. No 3 | 100 | 99 | 100 | 99 | 99 | 96 | 95 |
| Form. No 7 | 100 | 100 | 99 | 98 | 98 | 95 | 95 |
| Form. No 10 | 100 | 100 | 99 | 99 | 97 | 96 | 94 |
| Form. No 12 | 100 | 100 | 99 | 98 | 97 | 95 | 93 |
| Form. No 19 | 100 | 100 | 99 | 97 | 97 | 96 | 95 |
| AZASITE | 100 | 95 | 85 | 72 | 63 | 56 | 51 |

TABLE 1-continued

Stability study at 40° C. 6 months

| % AZT in | START | 1 month | 2 months | 3 months | 4 months | 5 months | 6 months |
|---|---|---|---|---|---|---|---|
| AZM-β-CD | | | | | | | |
| Form. No 23 | 100 | 93 | 90 | 87 | 84 | 80 | 74 |
| Form. No 25 | 100 | 94 | 92 | 87 | 85 | 81 | 74 |
| AZM-β-CD Metilate | | | | | | | |
| Form. No 31 | 100 | 91 | 82 | 74 | 65 | 60 | 53 |
| Form. No 33 | 100 | 90 | 80 | 71 | 63 | 56 | 52 |
| AZM-γ-CD | | | | | | | |
| Form. No 42 | 100 | 92 | 84 | 77 | 69 | 63 | 57 |
| Form. No 43 | 100 | 90 | 83 | 76 | 68 | 62 | 56 |
| AZM-SBE-γ-CD | | | | | | | |
| Form. No 52 | 100 | 93 | 86 | 75 | | | |
| Form. No 53 | 100 | 92 | 86 | 77 | | | |
| Form. No 54 | 100 | 92 | 85 | 75 | | | |
| AZYTER | 100 | 100 | 100 | 100 | 99 | 100 | 99 |

TABLE 2

Stability study at 25° C. up to 24 months

| % AZT in | START | 1 m. | 2 m. | 3 m. | 4 m.i | 5 m. | 6 m. | 8 m. | 12 m. | 18 m. | 24 m. |
|---|---|---|---|---|---|---|---|---|---|---|---|
| AZM-SBE-β-CD | | | | | | | | | | | |
| Form. No 2 | 100 | 100 | 100 | 100 | 100 | 99 | 99 | 98 | 97 | 95 | 95 |
| Form. No 3 | 100 | 99 | 100 | 99 | 99 | 100 | 99 | 98 | 98 | 97 | 97 |
| Form. No 7 | 100 | 100 | 100 | 99 | 100 | 99 | 99 | 99 | 98 | 96 | 96 |
| Form. No 10 | 100 | 100 | 100 | 99 | 99 | 99 | 98 | 98 | 97 | 97 | 97 |
| Form. No 12 | 100 | 100 | 99 | 99 | 98 | 98 | 97 | 97 | 96 | 95 | 95 |
| Form. No 19 | 100 | 100 | 100 | 99 | 98 | 99 | 98 | 98 | 98 | 97 | 97 |
| AZASITE | 100 | 99 | 98 | 97 | 97 | 95 | 92 | 90 | 86 | 79 | 69 |
| AZM-β-Hp-CD | | | | | | | | | | | |
| Form. No 23 | 100 | 99 | 98 | 98 | 97 | 97 | 96 | 95 | 94 | 88 | 78 |
| Form. No 25 | 100 | 100 | 99 | 99 | 98 | 97 | 96 | 96 | 94 | 90 | 79 |
| AZM-β-CD Metilate | | | | | | | | | | | |
| Form. No 31 | 100 | 100 | 100 | 99 | 97 | 97 | 96 | 93 | 91 | 78 | 65 |
| Form. No 33 | 100 | 99 | 99 | 98 | 97 | 97 | 95 | 92 | 90 | 81 | 69 |
| AZM-γ-CD | | | | | | | | | | | |
| Form. No 42 | 100 | 100 | 99 | 98 | 96 | 96 | 95 | 95 | 94 | 87 | 77 |
| Form. No 43 | 100 | 99 | 98 | 97 | 97 | 95 | 94 | 94 | 93 | 86 | 78 |
| AZM.SBE-γ-CD | | | | | | | | | | | |
| Form. No 52 | 100 | 99 | 99 | 98 | | | | | | | |
| Form. No 53 | 100 | 100 | 99 | 99 | | | | | | | |
| Form. No 54 | 100 | 99 | 98 | 98 | | | | | | | |
| AZYTER | 100 | 100 | 100 | 100 | 99 | 100 | 99 | 99 | 99 | 98 | 97 |

The stability studies at 25° C. confirm the preliminary results obtained at 40° C., i.e. that the chemical stability is comparable to that obtained for the commercial product in oily base, Azyter.

The stability studies at 4° C. are not shown because they were not considered significant compared to those at 40 and 25° C., as for the purposes of the present invention the central aspect is that the formulation of azithromycin proposed is stable at room temperature, both from the physical point of view and from that chemical point of view.

From the attached diagram of FIG. 1, in addition, it is clear that the formulations according to the invention, of which the graph shows a single example by way of example, solves the problem of stability if compared to Azasite, having a thermal stability profile similar to Azyter. In addition, the formulations according to the invention and also solve the problem of tolerability, that Azyter does not possess.

In the light of the studies carried out according to the invention it can be concluded that the presence of cyclodextrins, and in particular of SBE-β-CD (Captisol™) is fundamental for ensuring the stability of azithromycin at 25° C., and allowed to develop a formulation that does not require a refrigerated storage as for Azasite.

The present invention has been disclosed with particular reference to some specific embodiments thereof, but it should be understood that modifications and changes may be made by the persons skilled in the art without departing from the scope of the invention as defined in the appended claims.

The invention claimed is:

1. A topical ophthalmic preparation in aqueous solution containing azithromycin as active ingredient, solubilized and stabilized with sulfobutyl ether β-cyclodextrin (SBE-β-CD), said preparation having a pH comprised between 6.6 and 7.4 and a concentration of azithromycin, or of a pharmacologically acceptable salt or hydrate thereof, comprised between 0.5 and 2.5% by weight.

2. A topical ophthalmic preparation according to claim 1, wherein said SBE-β-CD is present in solution at a concentration comprised between 2% and 15% by weight.

3. A topical ophthalmic preparation according to claim 1, wherein the weight ratio of said SBE-β-CD to said azithromycin is comprised between 2.5:1 and 10:1.

4. A topical ophthalmic preparation according to claim 3, wherein the concentration of azithromycin is comprised between 1.0% and 2.5% by weight.

5. A topical ophthalmic preparation according to claim 3, wherein the concentration of said SBE-β-CD is comprised between 4% and 10% by weight.

6. A topical ophthalmic preparation according to claim 1, comprising, in addition, a viscosifying and/or mucoadhesive polymer.

7. A topical ophthalmic preparation according to claim 6, wherein said viscosifying and/or mucoadhesive polymer is selected from the group consisting of: carboxymethylcellulose, hydroxypropylcellulose, hyaluronic acid, chondroitin sulfate, alginic acid, natural polysaccharides, dextran, carbomers, carbopol, polyvinyl alcohol, polyethylene glycols, and xanthan gum.

8. A topical ophthalmic preparation according to claim 1, comprising, in addition, one or more osmotizing agents and a buffer system.

9. A topical ophthalmic preparation according to claim 1, comprising, in addition, one or more anti-oxidants, antimicrobials and/or preservatives.

10. A topical ophthalmic preparation according to claim 9, wherein said one or more anti-oxidants, antimicrobials and/or preservatives are selected from the group consisting of: ascorbic acid, sodium metabisulfite, tocopheryl acetate, lactoferrin, sodium edetate, benzalkonium chloride, polyhexanide, and TPGS.

11. A topical ophthalmic preparation in aqueous solution comprising an active ingredient, wherein the active ingredient is stabilized with sulfobutyl ether β-cyclodextrin (SBE-β-CD) and consists of azithromycin.

* * * * *